United States Patent [19]

Sarantakis

[11] 4,098,781
[45] Jul. 4, 1978

[54] POLYPEPTIDES WITH MORPHINE-LIKE ACTIVITY

[75] Inventor: Dimitrios Sarantakis, West Chester, Pa.

[73] Assignee: American Home Products Corporation, New York, N.Y.

[21] Appl. No.: 777,181

[22] Filed: Mar. 14, 1977

[51] Int. Cl.² .................... C07C 103/52; A61K 37/00
[52] U.S. Cl. ............................. 260/112.5 R; 424/177
[58] Field of Search ................. 260/112.5 R; 424/177

[56] References Cited
U.S. PATENT DOCUMENTS 4,038,222   7/1977   Li .................................. 260/112.5 R

OTHER PUBLICATIONS

G. Ungar, et al., Opiates and Endogenous Opioid Peptides, 1976, pp. 121–128.
D. H. Coy, et al., Biochem. and Biophys. Res. Commun., 73, 1976, pp. 632–638.

*Primary Examiner*—Delbert R. Phillips
*Attorney, Agent, or Firm*—Richard K. Jackson

[57] ABSTRACT

The polypeptides R-Tyr-Gly-Gly-Phe-Met-Thr-Ser-OH in which R is hydrogen or arginyl, or a non-toxic salt thereof, exert an analgesic effect in rats when injected into the lateral brain ventricle.

3 Claims, No Drawings

POLYPEPTIDES WITH MORPHINE-LIKE ACTIVITY

BACKGROUND OF THE INVENTION

Enkephalin, a natural opiate receptor agonist in the brain, has been identified [see Hughes et al., Nature, 256, 577 (1975)] as a mixture of two pentapeptides: H-Tyr-Gly-Gly-Phe-Met-OH (methionine-enkephalin) and H-Tyr-Gly-Gly-Phe-Leu-OH (leucine-enkephalin). Both peptides mimic the ability of morphine to block electrically evoked contractions of mouse vas deferens and guinea pig ileum, and both inhibit the stereospecific receptor binding of the opiate antagonist 3H-naloxone in brain homogenates.

It has been proposed that enkephalin receptors may be sites at which morphine-like drugs exert their analgesic activities, and that enkephalin may be the modulator or transmittor in brain systems for pain suppression or analgesia. It has been reported that methionine-enkephalin and leucine-enkephalin, when administered by injection in the brain ventricle in rats, induce a profound analgesia that is fully reversible by naloxone. [See Beluzzi et al., Nature, 260, 625 (1976)]. The enkephalins are inactive when administered peripherally, however, and it is believed that the enkephalins are rapidly destroyed by blood enzymes and/or are poorly transported across the blood-brain barrier.

The amino acid sequence of methionine-enkephalin is identical to that of the N-terminal portion of the C-fragment ($\beta$-endorphin or $\beta$-LPH[61-19]) of the peptide $\beta$-lipotropin, which is found in large concentrations in the pituitary and in much lower concentrations in the brain. Other naturally-occuring fragments of $\beta$-lipotropin are known, for example: $\alpha$-endorphin ($\beta$-LPH[61$\iota$]) and $\gamma$-endorphin ($\beta$-LPH[61-77]). Both $\beta$-lipotropin and the endorphins show morphine-like properties in various test systems, and it has been suggested that methionine-enkephalin is a breakdown product of the large opiate-like peptides. Enkephalin, its relationship to $\beta$-lipotropin and the endorphins, and the pharmacological properties thereof, are reviewed in an article by Iversen et al., Nature, 262, 738 (1976). Recent developments are also described in detail in the "Proceedings of the International narcotics Research Club Meeting, Aberdeen, U. K., July 19-22, 1976", published in OPIATES AND ENDOGENOUS OPIOID PEPTIDES, North Holland Publishing Company, Amsterdam, 1976.

Various structural variations of methionine-enkephalin and leucine-enkephalin are described in the literature. For example, the pentapeptide H-Tyr-Gly-Gly-Phe-Thr-OH, wherein the fifth amino acid residue (methionine or leucine) is replaced by threonine, is described by Chang et al., Life Sciences, 18, 1473 (1976).

DESCRIPTION OF THE INVENTION

The present invention related to a structural modification of methionine-enkephalin wherein H-Arg is optionally introduced N-terminally and Thr-Ser-OH is introduced C-terminally. In accordance with the invention there is provided a polypeptide of the formula:

R-Tyr-Gly-Gly-Phe-Met-Thr-Ser-OH           I in which R is hydrogen or arginyl, or a non-toxic salt thereof. All chiral amino acid residues identified in Formula I, and in the other formulae depicted herein, are in the natural or L-configuration.

The polypeptides of Formula I, or a non-toxic salt thereof, exert an analgesic effect as demonstrated in rats using the rat-tail flick method of D'Amour and Smith [D'Amour and Smith, J. Pharmacol. Exp. Ther., 72, 74 (1941)] when they are injected directly into the lateral brain ventricle. In this test method, which is a standard test for analgesia, a light beam is focused on the tip of the rat's tail, and the pain threshold of the animal is measured by the latency of the rat to remove his tail from the noxious heat source. When tested by the rat-tail flick method by intracerebroventricular injection, according to the procedure of Belluzzi et al., Nature, 260, 625 (1976), the polypeptides of this invention produced the effects set forth in Table I.

TABLE I

| Drug* | Dose | No. of Rats | Mean Latency ± SEM | | Mean % Change ± SEM |
|---|---|---|---|---|---|
| | | | Baseline | Drug | |
| Ringer's Solution (pH 4.0) | — | 13 | 4.02 ± 0.20 | 4.27 ± 0.28 | 6.6 ± 6.9 |
| H-Arg-Tyr-Gly-Gly-Gly-Phe-Met-Thr-Ser-OH | 100 μg | 3 | 3.43 ± 0.05 | 5.29 ± 1.10 | 55.13 ± 51.71 |
| | 50 μg | 3 | 3.55 ± 0.13 | 6.18 ± 0.55 | 74.13 ± 15.56 |
| | 25 μg | 1 | 3.54 | 6.01 | 69.60 |
| H-Tyr-Gly-Gly-Phe-Met-The-Ser-OH | 100 μg | 2 | 3.47 ± 0.01 | 5.43 ± 0.22 | 56.42 ± 6.72 |
| | 50 μg | 1 | 3.50 | 6.38 | 82.00 |
| Methionine-Enkephalin | 100 μg | 24 | 3.83 ± 0.14 | 5.19 ± 0.31 | 37.2 ± 8.8 |
| Morphine | 10 μg | 7 | 3.96 ± 0.42 | 6.59 ± 0.73 | 65.4 ± 9.1 |

*All drugs were dissolved in 10 ml. of Ringer's solution and injected into the lateral ventricle through permanently-indwelling cannulae.

The results in Table I show that injection of the polypeptides of this invention into the lateral brain ventricle produced an increase in pain threshold as indicated by the significant difference between the mean % change in latency for the drug (drug minus baseline) and the mean % change in latency for the vehicle (Ringer's solution minus baseline). It has been found that the polypeptides of this invention exhibit weak binding to opiate receptors in vitro and are capable of displacing 3H-naloxone from binding sites in rat brain homogenates, activity consistent with an opiate-like analgesic effect.

Also contemplated by this invention are the salts of the polypaptides of Formula I with non-toxic, pharmaceutically acceptable acids. Suitable acids, both organic and inorganic, will be readily apparent to one skilled in the art, for example: hydrochloric, hydrobromic, sulfonic, phosphoric, maleic, acetic, citric, benzoic, succinic, malic, ascorbic, and the like. The salts are prepared and isolated by conventional methods.

The symbols used for representing the amino acid residues in Formula I and in the other formulae employed herein are defined according to the IUPAC-IUB Commission on Biochemical Nomenclature Recommendations (1971), Archives of Biochemistry and Biophysics, 150, 1–8 (1972).

The polypeptides of Formula I are prepared by solid-phase techniques well known in the art of peptide chemistry. The method of synthesis is illustrated in the following examples.

EXAMPLE 1

Tert-Butyloxycarbonyl-O-2,6-Dichlorobenzyl-L-Tyrosyl-Glycyl-Glycyl-L-Phenylalanyl-L-Methionyl-D-Benzyl-L-Threonyl-O-Benzyl-L-Seryl-Hydroxymethyl-Polystyrene Chloromethylated polystyrene resin (Lab Systems, Inc.) was esterfied with Boc-Ser(Bzl)-OH according to Gisin, Helv. Chim. Acta, 56, 1976 (1973). The polystyrene ester (9 g.) was treated according to Schedule A for the incorporation of Boc-Thr(Bzl)-OH, Boc-Met-OH, Boc-Phe-OH, Boc-Gly-OH, Boc-Gly-OH and Boc-Tyr($Cl_2$Bzl)-OH to afford the title peptido resin.

SCHEDULE A

1. Wash with $CH_2Cl_2 \times 3$.
2. Treat with TFA-$CH_2Cl_2$-DTE (1:2:0.5%) for 5 min.
3. Treat with TFA-$CH_2Cl_2$-DTE (1:2:0.5%) for 25 min.
4. Wash with $CH_2Cl_2 \times 3$.
5. Wash with DMF.
6. Treat with 12% TEA in DMF twice for 3 min.
7. Wash with DMF.
8. Wash with $CH_2Cl_2 \times 3$.
9. Treat with 4 equivalents of the corresponding amino acid derivative in $CH_2Cl_2$-DMF and 4 equivalents of N-hydroxybenzotriazole and stir for 5 min.
10. Add in two portions 5 equivalents of DIC dissolved in $CH_2Cl_2$ and over a period of 30 minutes. Reaction time 12–18 hours.
11. Wash with DMF $\times$ 3.
12. Wash with $CH_2Cl_2 \times 3$.
13. Test ninhydrin reaction according to Kaiser et al., Annal. Biochem., 34, 595 (1970). In case of incomplete reaction repeat lines 9 to 13 as above.

EXAMPLE 2

L-Tyrosyl-Glycyl-Glycyl-L-Phenylalanyl-L-Methionyl-L-Threonyl-L-Serine Acetate

The peptido resin of the previous example was mixed with thioanisole and treated with a ten-fold volume of liquid HF for 40 minutes in an ice bath with exclusion of air. The excess HF was evaporated in Vacuo as fast as possible and the residue taken in dil. aq. acetic acid, filtered and the filtrate extracted with ether. The aqueous phase was lyophilized to yield a crude product containing the title product.

This crude material was chromatographed through a Sephadex G-10 column and eluted with 10% aq. acetic acid. The main peak of the elution was collected and lyophilized to yield the title heptapeptide.

$R_f$(BWA) 0.50, $R_f$(BWAP) 0.64

Amino Acid Analysis: Thr (1) 0.96; Ser. (1) 0.86; Gly (2) 2.16; Met (1) 0.95; Tyr (1) 0.88; Phe (1) 1.

EXAMPLE 3

Tert-Butyloxycarbonyl-$N^g$-Tosyl-L-Arginyl-O-2,6-Dichlorobenzyl-L-Tyrosyl-Glycyl-Glycyl-L-Phenylalanyl-L-Methionyl-O-Benzyl-L-Threonyl-O-Benzyl-L-Seryl-Hydroxymethyl Polystyrene To the peptido resin of Example 1 was added Boc-Arg(Tos)-OH in accordance with Schedule A to afford the title product.

EXAMPLE 4

L-Arginyl-L-Tyrosyl-Glycyl-Glycyl-L-Phenylalanyl-L-Methionyl-L-Threonyl-L-Serine The peptido resin of the previous examples was mixed with anisole and treated with liquid HF for 40 minutes in an ice-bath. The excess HF was removed under vacuo as fast as possible and the residue was taken in 2 M-aq. AcOH, filtered and the filtrate washed with ether. The aqueous layer was lyophilized to yield 2.6 g. of solid.

The crude material was applied onto a column (2.5 $\times$ 96 cm.) of Sephadex G-10 and eluted with 5% aq. AcOH. The material which emerged between fractions (5.3 ml.) 33 to 55 was pooled and lyophilized to yield 2.5 g. white solid. Part of the material (1.5 g.) was applied again onto a column (2.5 $\times$ 160 cm.) of Sephadex G-25 and eluted with 5% aq. AcOH. The compound which emerged between fractions (5.1 ml.) 99–101 was pooled and lyophilized to yield 158 mg. of the title compound.

$R_f$(n-butanol-water-gl. acetic acid, 4:5:1) 0.58

$R_f$ (n-butanol-water-gl. acetic acid, pyridine, 30:24:6:20) 0.66

Amino Acid Analysis: Thr (1) 1.04; Ser (1) 0.99; Gly (2) 2.16; Met (1) 0.85; Tyr (1) 0.88 Phe (1) 1, Arg (1) 1.05

What is claimed is:

1. A polypeptide of the formula:

R-Tyr-Gly-Gly-Phe-Met-Thr-Ser-OH in which R is hydrogen or arginyl, or a non-toxic salt thereof, all optically active amino acids being of the L-configuration.

2. The compound of claim 1 which is:

H-Tyr-Gly-Gly-Phe-Met-Thr-Ser-OH or a non-toxic salt thereof.

3. The compound of claim 1 which is:

H-Arg-Tyr-Gly-Gly-Phe-Met-Thr-Ser-OH or a non-toxic salt thereof.

* * * * *